(12) United States Patent
Kim et al.

(10) Patent No.: US 12,357,985 B2
(45) Date of Patent: Jul. 15, 2025

(54) AMPLIFICATION/DETECTION KIT, PHOTOTHERMAL PCR AMPLIFICATION METHOD AND MICROORGANISM DETECTION METHOD USING THE SAME

(71) Applicant: Gwangju Institute of Science and Technology, Gwangju (KR)

(72) Inventors: Min Gon Kim, Gwangju (KR); Bo Bin Lee, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 193 days.

(21) Appl. No.: 17/100,352

(22) Filed: Nov. 20, 2020

(65) Prior Publication Data

US 2022/0088587 A1    Mar. 24, 2022

(30) Foreign Application Priority Data

Sep. 18, 2020 (KR) ........................ 10-2020-0120623

(51) Int. Cl.
    *B01L 3/00*      (2006.01)
    *C12Q 1/6851*      (2018.01)
    *G01N 33/569*      (2006.01)

(52) U.S. Cl.
    CPC .......... *B01L 3/5027* (2013.01); *C12Q 1/6851* (2013.01); *G01N 33/569* (2013.01);
    (Continued)

(58) Field of Classification Search
    CPC ..... B01L 2300/0645; B01L 2300/0819; B01L 2300/0829; B01L 2300/0851;
    (Continued)

(56) References Cited

U.S. PATENT DOCUMENTS

| | | | |
|---|---|---|---|
| 2011/0081686 A1* | 4/2011 | Manthorpe | ............. B01L 7/525 |
| | | | 435/286.1 |
| 2016/0172153 A1* | 6/2016 | Damiano, Jr. | ........ H01J 37/261 |
| | | | 250/443.1 |

(Continued)

FOREIGN PATENT DOCUMENTS

| | | |
|---|---|---|
| JP | 2019530459 | 10/2019 |
| KR | 1020170106995 | 9/2017 |

(Continued)

OTHER PUBLICATIONS

Mark et al ("Microfluidic lab-on-a-chip platforms: requirements, characteristics and applications") Chem. Soc. Rev., 2010,39, 1153-1182 (Year: 2010).*

(Continued)

*Primary Examiner* — Jennifer Wecker
*Assistant Examiner* — Jonathan Bortoli
(74) *Attorney, Agent, or Firm* — CANTOR COLBURN LLP

(57) ABSTRACT

Disclosed is an amplification/detection kit comprising: a sample pad on which a PCR reaction solution is placed; a transfer pad positioned in contact with the sample pad; a reaction pad into which the PCR reaction solution flowing from the sample pad through the transfer pad flows and which includes a gold thin film deposited on a first surface; and a sealing tape configured to cover and seal a first surface of the transfer pad and a first surface of the reaction pad.

6 Claims, 12 Drawing Sheets

Specification includes a Sequence Listing.

(52) U.S. Cl.
CPC ............... *B01L 2200/10* (2013.01); *B01L 2300/0816* (2013.01); *B01L 2300/1861* (2013.01)

(58) Field of Classification Search
CPC ....... B01L 2300/165; B01L 2400/0427; B01L 3/50273; B01L 3/502792
See application file for complete search history.

(56) References Cited

U.S. PATENT DOCUMENTS

| | | | | |
|---|---|---|---|---|
| 2017/0233797 | A1* | 8/2017 | Ramsey | B01L 7/52 506/9 |
| 2018/0080064 | A1* | 3/2018 | Lee | B01L 7/52 |
| 2019/0032114 | A1* | 1/2019 | Trivedi | B01L 3/5027 |
| 2019/0299207 | A1 | 10/2019 | Lee et al. | |
| 2022/0062888 | A1* | 3/2022 | Kwon | B01L 3/502715 |

FOREIGN PATENT DOCUMENTS

| | | | | |
|---|---|---|---|---|
| KR | 1020180034579 | | 4/2018 | |
| KR | 1020180073725 | | 7/2018 | |
| KR | 20180101099 | | 9/2018 | |
| KR | 1020190070267 | | 6/2019 | |
| KR | 20190096500 | * | 8/2019 | ............ B01L 3/00 |
| KR | 1020190096500 | | 8/2019 | |
| KR | 1020190136909 | | 12/2019 | |
| KR | 102111024 | | 5/2020 | |
| WO | WO-2016121929 A1 | * | 8/2016 | ............ C12M 1/00 |

OTHER PUBLICATIONS

Cho et al, ("Nanophotonic Cell Lysis and Polymerase Chain Reaction with Gravity-Driven Cell Enrichment for Rapid Detection of Pathogens") ACS Nano 2019 13 (12), 13866-13874 (Year: 2019).*
Kaur et al ("A modular paper-and-plastic device for tuberculosis nucleic acid amplification testing in limited-resource settings"). Sci Rep 9, 15367 (Year: 2019).*
Translation of KR20190096500 (Year: 2019).*
Translation of KR20170094616A (Year: 2017).*
Tomás et al "Development of a Gold Nanoparticle-Based Lateral-Flow Immunoassay for Pneumocystis Pneumonia Serological Diagnosis at Point-of-Care". Front Microbiol. Dec. 19, 2019;10:2917. doi: 10.3389/fmicb.2019.02917. (Year: 2019).*
Alexander et al, "Simulation and experimental investigation of optical transparency in gold island films," Opt. Express 21, 4126-4138 (2013) (Year: 2013).*
Kaur, et al A modular paper-and-plastic device for tuberculosis nucleic acid amplification testing in limited-resource settings. Sci Rep 9, 15367 (2019) (Year: 2019).*
Zhang ("Miniaturized PCR chips for nucleic acid amplification and analysis: latest advances and future trends"). Nucleic Acids Res. 2007;35(13):4223-37. doi: 10.1093/nar/gkm389. Epub Jun. 18, 2007. (Year: 2007).*
WO2016121929A1 English translation (Year: 2024).*
Youngung Seok, et al., "Lab-on-paper for all-in-one molecular diagnostics (LAMDA) of zika, dengue, and chikungunya virus from human serum",Biosensors and Bioelectronics, (2020), vol. 165, pp. 1-8.

* cited by examiner 1) 100 nm, 2) 40 nm, 3) 20nm, 4) 10 nm, 5) 5 nm 1) 10 Sec, 2) 15 Sec, 3) 20 Sec, 4) 25 Sec 1) Control, 2) 0.1 pg/ul, 3) 1 pg/ul, 4) 10 pg/ul, 5) 100 pg/ul

AMPLIFICATION/DETECTION KIT, PHOTOTHERMAL PCR AMPLIFICATION METHOD AND MICROORGANISM DETECTION METHOD USING THE SAME

CROSS-REFERENCE TO RELATED APPLICATION

This application claims priority to and the benefit of Korean Patent Application No. 10-2020-0120623 filed in the Korean Intellectual Property Office on Sep. 18, 2020, the entire contents of which are incorporated herein by reference.

SEQUENCE LISTING

This application includes a sequence listing submitted as an ASCII text file created Dec. 17, 2020, named 8NM321302.TXT and having a file size of 4.00 KB; the sequence listing is incorporated by reference herein.

BACKGROUND OF THE INVENTION

(a) Field of the Invention

The present invention relates to an amplification/detection kit, a photothermal PCR amplification method and a microorganism detection method using the same.

(b) Description of the Related Art

In order to initially detect and treat, particularly, viral diseases such as Ebola, MERS, and influenza among world famous diseases, rapid and accurate diagnosis of these diseases is very important. In order to diagnose these viral diseases with high sensitivity, it is required to amplify genes by polymerase chain reaction (PCR). A general PCR method is performed by repeating the binding and amplification of a polymerase and a gene in a solution in multiple cycles of temperature circulation. The temperature circulation should be performed by increasing and then decreasing the temperature of a PCR reaction solution by heating and cooling a plastic tube containing the PCR reaction solution with a heating block, but may require an hour or more due to poor heat transfer efficiency of the plastic tube.

Recently, research on application methods for rapid PCR for fatal diseases where early diagnosis is important has been actively conducted. When increasing and then decreasing the temperature is defined as one cycle of temperature circulation, currently, a technology of taking about 10 minutes for 30 cycles of temperature circulation has been developed. However, most of the developed equipment are optimized under laboratory conditions, and are limited in a use environment and have poor portability due to heavy (20 Kg or more) and high energy consumption (800 to 1000 W).

The above information disclosed in this Background section is only for enhancement of understanding of the background of the invention, and therefore it may contain information that does not form the prior art that is already known in this country to a person of ordinary skill in the art.

SUMMARY OF THE INVENTION

The present invention has been made in an effort to provide a light and portable amplification/detection kit, an amplification/detection kit capable of performing PCR amplification and detecting a microorganism using the same, and a photothermal PCR amplification method and a microorganism detection method using the same.

An exemplary embodiment of the present invention provides an amplification/detection kit including: a sample pad on which a PCR reaction solution is placed; a transfer pad positioned in contact with the sample pad; a reaction pad into which the PCR reaction solution flowing from the sample pad through the transfer pad flows and which includes a gold thin film deposited on a first surface; and a sealing tape configured to cover and seal a first surface of the transfer pad and a first surface of the reaction pad.

The gold thin film may be formed by depositing gold on the pad with an electron-beam.

The pad may be a glass fiber pad. The sample pad and the transfer pad may be glass fiber pads.

Another embodiment of the present invention provides a photothermal PCR amplification method using an amplification/detection kit including a gold thin film formed by depositing gold on a pad with an electron-beam, including the steps: irradiating a laser having a predetermined intensity and a predetermined wavelength to the gold thin film for a first period; stopping the laser irradiation to the gold thin film for a second period subsequent to the first period; and repeating the irradiating of the laser and the stopping of the laser irradiation at a predetermined number of times.

Yet another embodiment of the present invention provides a microorganism detection method using an amplification/detection kit including a gold thin film formed by depositing gold on a pad with an electron-beam, comprising the steps: irradiating a laser having a predetermined intensity and a predetermined wavelength to the gold thin film for a first period; stopping the laser irradiation to the gold thin film for a second period subsequent to the first period; repeating the steps of irradiating the laser and stopping the laser irradiation at a predetermined number of times; and measuring light emitted from the amplification/detection kit after the repeating is terminated.

For the first period, heat may be transferred to the pad from the gold thin film to isolate DNA of a microorganism from a PCR reaction solution.

For the second period, the heat may be emitted from the pad and DNA polymerization and primer annealing of the microorganism may occur in the PCR reaction solution.

According to an embodiment of the present invention, it is possible to provide a light and portable amplification/detection kit, an amplification/detection kit capable of performing PCR amplification and detecting a microorganism using the same, and a photothermal PCR amplification method and a microorganism detection method using the same.

DETAILED DESCRIPTION OF THE EMBODIMENTS

Figure 1:
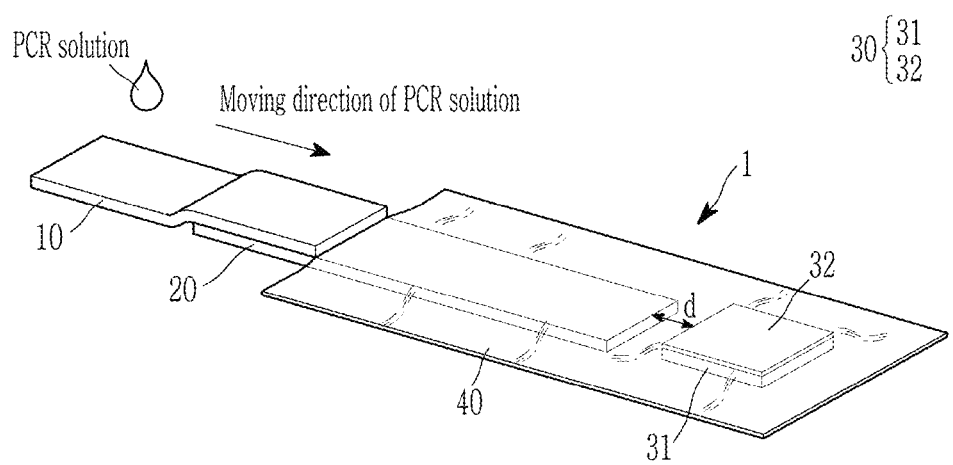
FIG. 1 is a diagram illustrating an amplification/detection kit according to an exemplary embodiment.

An amplification/detection kit according to an embodiment may perform PCR quickly within about 10 minutes by a simple method and have good portability and high applicability. In addition, it is possible to have low energy consumed during the PCR process using the amplification/detection kit, and perform gene amplification and high-sensitivity quantitative measurement through PCR using the amplification/detection kit.

Hereinafter, exemplary embodiments disclosed in this specification will be described in detail with reference to the accompanying drawings and the same or similar components are denoted by the same reference numerals, and duplicated description thereof will be omitted. Suffixes "module", and/or "unit" for components used in the following description are given or mixed in consideration of easy preparation of the specification only and do not have their own distinguished meanings or roles. Further, in describing an exemplary embodiment disclosed in the present disclosure, a detailed description of related known technologies will be omitted if it is decided that the detailed description makes the gist of the exemplary embodiment of the present disclosure unclear. Also, it should be understood that the appended drawings are intended only to help understand embodiments disclosed in the present disclosure, but do not limit the technical principles and scope of the present invention and include all of the modifications, equivalents or substitutes included in the idea and the technical scope of the present invention.

Terms including an ordinal number, such as first and second, are used for describing various components, but the components are not limited by the terms. The terms are used only to discriminate one component from another component.

It should be understood that, when it is described that a component is "connected to" or "access" the other component, the component may be directly connected to or access the other component or another component may be present therebetween. In contrast, it should be understood that, when it is described that a component is "directly connected to" or "directly access" the other component, another component is not present therebetween.

In the present application, it should be understood that the term "comprising" or "having" indicates that a feature, a number, a step, an operation, a component, a part or a combination thereof described in the specification is present, but does not exclude a possibility of presence or addition of one or more other features, numbers, steps, operations, components, parts or combinations thereof, in advance.

An amplification/detection kit for photothermal PCR amplification according to an embodiment includes a glass fiber membrane and a gold thin film deposited directly on the membrane. A part wet with a PCR reaction solution in the membrane is sealed, and a 785 nm laser is irradiated to the gold thin film for a predetermined irradiation period, and the irradiation is stopped during a predetermined stop period. As such, when the irradiation and irradiation stop are repeated, and the temperature circulation in the membrane is repeated, PCR amplification is performed inside the membrane. The PCR reaction solution refers to a mixture of a PCR solution and a sample required for PCR amplification.

FIG. 1 is a diagram illustrating an amplification/detection kit according to an exemplary embodiment.

An amplification/detection kit 1 includes a sample pad 10, a transfer pad 20, a reaction pad 30, and a sealing tape 40.

The PCR reaction solution is placed on the sample pad 10. The sample pad 10 is made of a glass fiber material.

The transfer pad 20 is placed in contact with the sample pad 10, and the PCR reaction solution flows from the sample pad 10 through the transfer pad 20. A part of the sample pad 10 and a part of the transfer pad 20 overlap with and come into contact with each other in a direction perpendicular to the direction in which the PCR reaction solution flows. In FIG. 1, a part of the sample pad 10 is shown to be positioned on a part of the transfer pad 20. The transfer pad 20 is also made of the same glass fiber material as the sample pad 10.

The PCR reaction solution flowing through the transfer pad 20 from the sample pad 10 flows into the reaction pad 30. In the reaction pad 30, gold is directly deposited on the pad 31 made of the glass fiber material to form a gold thin film 32. Gold is deposited on the upper surface of the pad 31, and a portion of the pad 31 to which gold does not penetrate remains as the glass fiber. Since the glass fiber has a structure in which glass fiber strands are entangled, spaces having sizes of tens to several hundreds μm exist inside the pad 31. Since the size of the empty spaces inside the pad 31 is sufficiently larger than that of the enzyme, PCR amplification reaction occurs in these spaces.

The sealing tape 40 covers a peripheral area of the amplification/detection kit 1 together with the upper surface of the transfer pad 32 and the upper surface of the reaction pad 30 to seal the transfer pad 32 and the reaction pad 30. In FIG. 1, the sealing tape 40 is formed with a wider width than those of the transfer pad 20 and the reaction pad 30 and a length enough to cover the transfer pad 20 and the reaction pad 30. The size and shape illustrated in FIG. 1 are just an example, and the sealing tape 40 may be formed in a size and shape enough to cover the transfer pad 20 and the reaction pad 30.

In FIG. 1, since the transfer pad 20 and the reaction pad 30 are spaced apart from each other at a predetermined distance d, a space exists between the two pads. The distance (d) is about 1 mm, and the space between the two pads is an empty space surrounded by the sealing tape 40, and is a space for positioning a sealing frame 50 (see FIG. 2) surrounding the reaction pad 30 for PCR amplification. The PCR reaction solution may be sufficiently added to the sample pad 10 so that the PCR reaction solution flows out from the transfer pad 30 to be transferred to the reaction pad 40 through this space.

According to the structure of the amplification/detection kit 1 illustrated in FIG. 1, the PCR reaction solution added to the sample pad 10 flows through the transfer pad 20 by a capillary phenomenon, and the PCR reaction solution passing through the transfer pad 20 may be absorbed in the reaction pad 30 through a capillary phenomenon. Then, the PCR reaction solution required for photothermal PCR amplification is collected in the reaction pad 30.

Hereinafter, a photothermal PCR amplification process will be described with reference to FIGS. 2 and 3.

Figure 2:
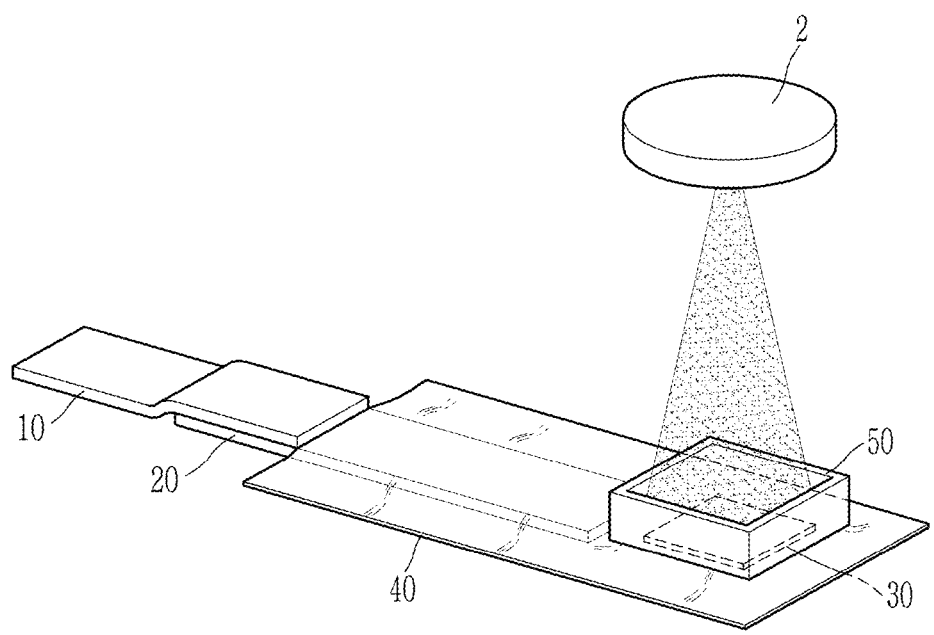
FIG. 2 is a diagram schematically illustrating laser irradiation for photothermal PCR amplification in the amplification/detection kit.

FIG. 2 is a diagram schematically illustrating laser irradiation for photothermal PCR amplification in the amplification/detection kit.

Figure 3:
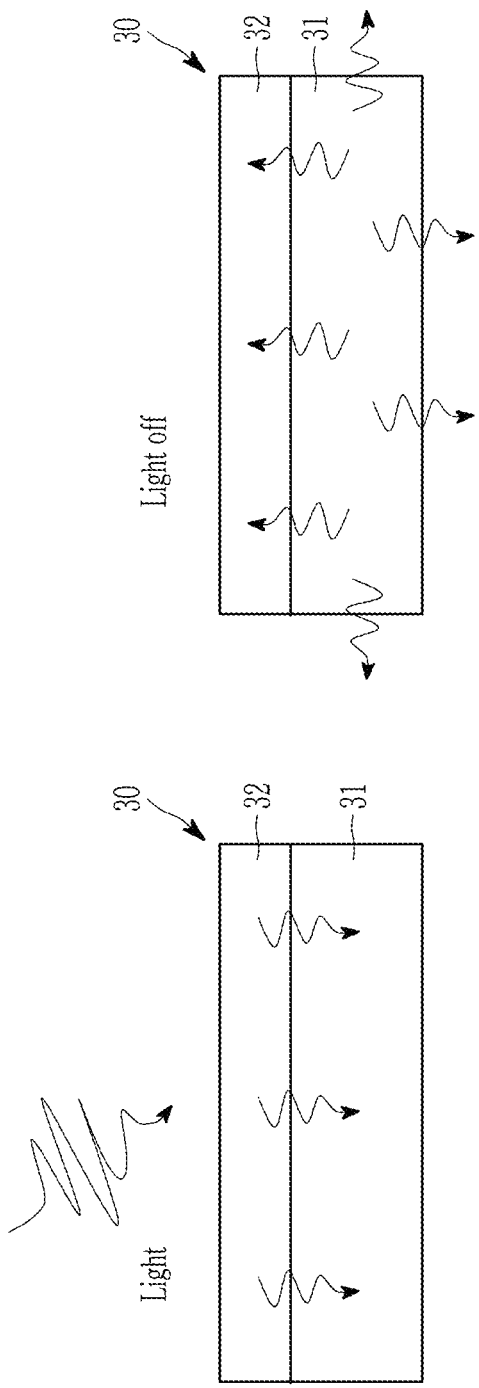
FIG. 3 is a diagram schematically illustrating states of reaction pads during laser irradiation and when the laser irradiation is stopped.

FIG. 3 is a diagram schematically illustrating the states of the reaction pad during laser irradiation and when the laser irradiation is stopped.

The laser device 2 irradiates a laser having a wavelength of 785 nm to the reaction pad 30. At this time, as illustrated in FIG. 2, the sealing frame 50 surrounds the reaction pad 30. In the photothermal PCR amplification process, the reaction pad is pressed with the sealing frame 50 to withstand the internal pressure of the reaction pad 30 caused by high temperature.

The laser device 2 irradiates the laser during a heating period and stops laser irradiation during a cooling period. The combined period of the heating and cooling periods is one cycle of temperature circulation for photothermal PCR amplification. The laser device 2 repeats the temperature circulation at a predetermined number of times, and the photothermal PCR amplification is performed according to the temperature circulation at a predetermined number of times.

As illustrated in FIG. 3A, when the laser is irradiated on the gold thin film 32 during the heating period, the gold thin film 32 may absorb light and generate heat. The heat generated by the gold thin film 32 is transferred to the pad 31. In the PCR amplification, the temperature inside the pad 31 rises to a temperature of about 95° C. or higher required for the DNA separation step for a predetermined period.

As illustrated in FIG. 3B, if the laser is not irradiated during the cooling period, heat generation is stopped from the gold thin film 32 and heat is released from the pad 31, so that the temperature inside the pad 31 decreases to a temperature required for DNA polymerization and primer annealing. This operation occurs during one cycle of temperature circulation, and the temperature circulation is repeated at a predetermined number of times to perform the photothermal PCR amplification.

The pad made of fiber glass is stronger to heat than pads made of other materials. In one embodiment, gold has been deposited directly on the glass fiber pad in an electron-beam (e-beam) method to fabricate the reaction pad 30. At this time, when determining the thickness of the gold thin film 32 in the reaction pad 30, the heat transfer efficiency and the temperature increase efficiency of the PCR reaction solution have been considered.

Figure 4:
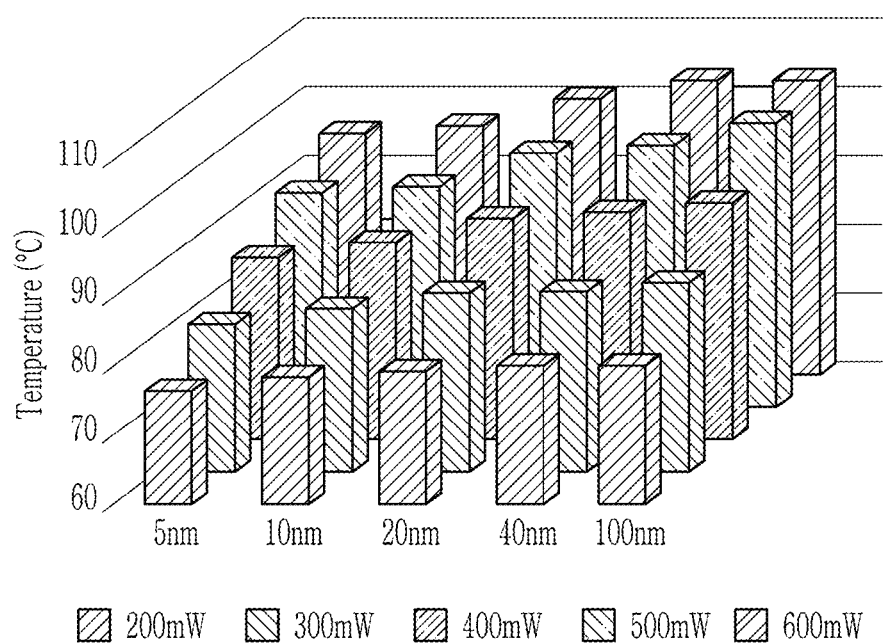
FIG. 4 is a graph showing changes in temperature characteristics in the reaction pad according to a gold thin film thickness and a laser intensity.

FIG. 4 is a graph showing changes in temperature characteristics in the reaction pad according to a gold thin film thickness and a laser intensity.

Figure 5:
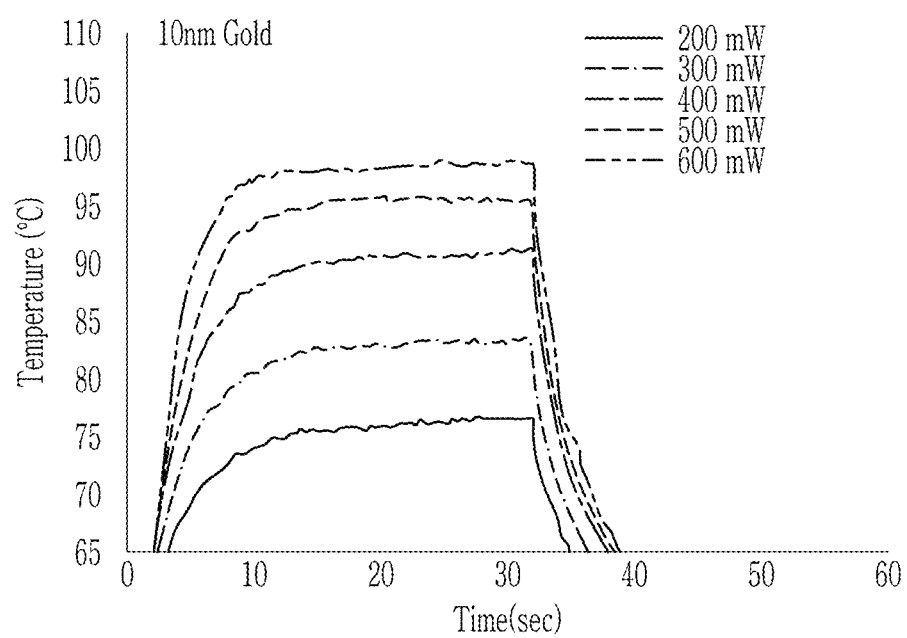
FIG. 5 is a graph showing temperature characteristics in the reaction pad according to a laser intensity in a 10 nm-thick gold thin film.

FIG. 5 is a graph showing temperature characteristics in the reaction pad according to a laser intensity in a 10 nm-thick gold thin film.

Figure 6:
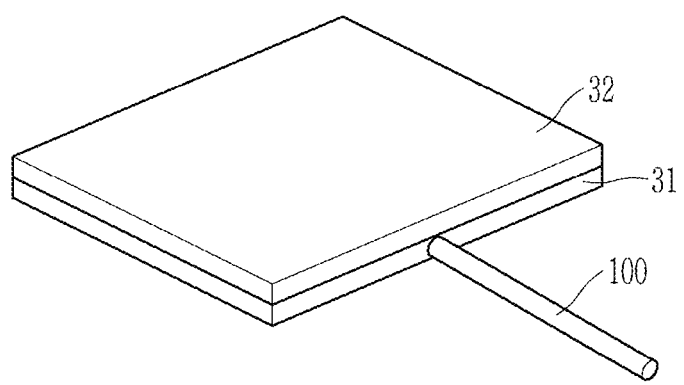
FIG. 6 is a diagram illustrating a method for measuring a temperature of a reaction pad for temperature measurement.

FIG. 6 is a diagram illustrating a method for measuring a temperature of a reaction pad for temperature measurement.

As illustrated in FIG. 6, a thermocouple temperature sensor 100 is inserted into the pad 31 in the reaction pad 30. The temperature inside the pad 31 is measured using the thermocouple temperature sensor 100, and the heat transfer to the PCR reaction solution inside the pad 31 and the temperature increase efficiency of the PCR reaction solution may be detected according to the irradiated laser intensity and the thickness of the gold thin film 32. In FIG. 5, the PCR reaction solution is injected into the pad 31.

In FIG. 4, when the gold thin film 32 is 10 nm thick, changes in temperature of the PCR reaction solution inside the pad 31 are illustrated when irradiating a 785 nm laser to the gold thin film 32 with intensities of 200 mW, 300 mW, 400 mW, 500 mW, and 600 mW, respectively.

As illustrated in FIG. 4, it can be seen that when the laser intensity is 600 mW, the temperature is saturated only in 5 seconds, and reaches a maximum temperature by laser irradiation for 10 seconds for all intensities.

In FIG. 5, when the thickness of the gold thin film 32 is 5 nm, 10 nm, 20 nm, 40 nm, and 100 nm, respectively, a maximum temperature is illustrated when irradiating a 785 nm laser with an intensity of 200 mW, 300 mW, 400 mW, 500 mW, and 600 mW for 10 seconds, respectively. The laser irradiation period may be 10 seconds.

As illustrated in FIG. 5, the thicker the gold thin film, the higher the heat generation efficiency. However, when irradiating the laser with the intensity of 600 mW regardless of the thickness of the gold thin film 32, a maximum temperature higher than 95° C. required for PCR amplification may be obtained regardless of the thickness.

Figure 7:
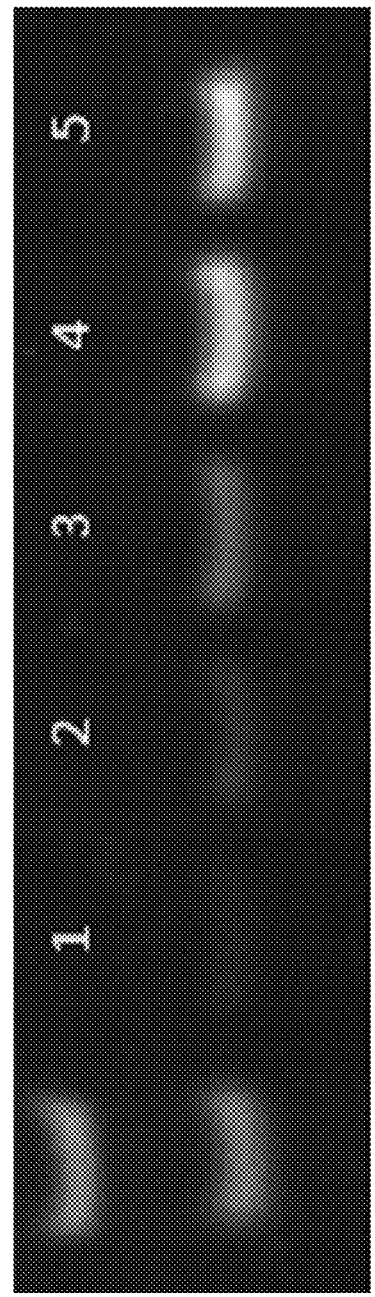
FIG. 7 is a diagram illustrating a PCR amplification result according to a thickness of the gold thin film.

FIG. 7 is a diagram illustrating a PCR amplification result according to a thickness of the gold thin film.

The PCR result illustrated in FIG. 7 is a result of confirming a result of irradiating the 785 nm laser with the intensity of 600 mW for 5 seconds and performing photothermal PCR amplification for a sufficient time while stopping the laser irradiation for 30 seconds through gel electrophoresis.

As illustrated in FIG. 7, it can be seen that the higher the thickness of the gold thin film 32, the lower the PCR efficiency. Based on the result illustrated in FIG. 6, a gold thin film 32 having a thickness of 10 nm thicker is applied to the embodiment in consideration of heat generation efficiency among gold thin films having thicknesses of 10 nm and 5 nm having similar PCR amplification efficiency.

The photothermal PCR amplification is performed using the reaction pad 30 including the 785 nm laser having the intensity of 600 mW and the gold thin film 32 having the thickness of 10 nm. During one cycle of temperature circulation, while the heating period is 5 seconds and the cooling period is changed, the photothermal PCR amplification is performed. For example, the cooling period is changed to 10 seconds, 15 seconds, 20 seconds, and 25 seconds. The photothermal PCR amplification is performed while repeating the temperature circulation cycle 25 times.

Figure 8:
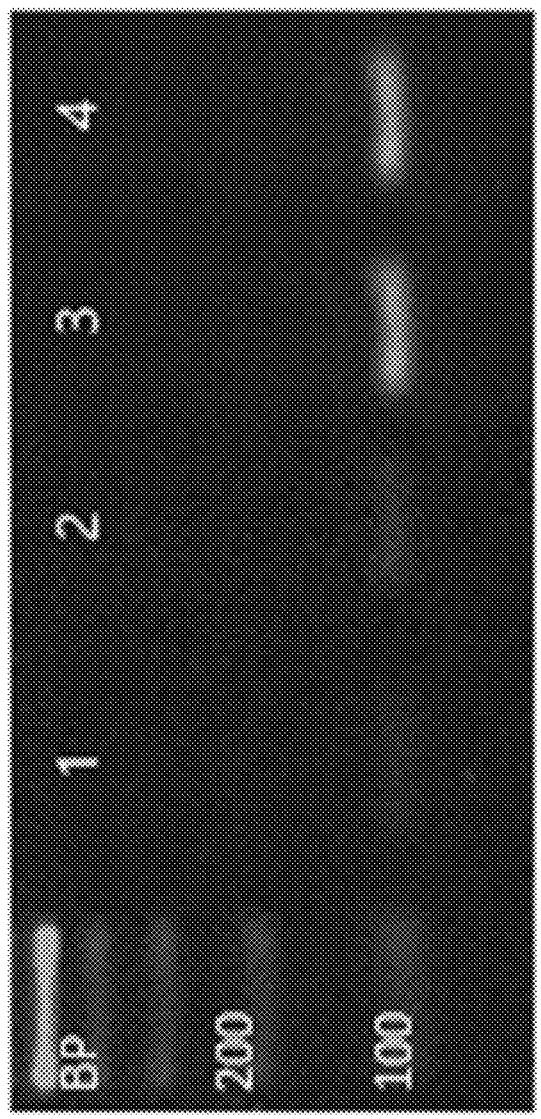
FIG. 8 is a diagram illustrating a photothermal PCR amplification result when cooling periods are 10 seconds, 15 seconds, 20 seconds, and 25 seconds, respectively.

FIG. 8 is a diagram illustrating a photothermal PCR amplification result when cooling periods are 10 seconds, 15 seconds, 20 seconds, and 25 seconds, respectively.

In FIG. 8, when the cooling period varies, a result of detecting the photothermal PCR amplification result according to each cooling period by gel electrophoresis is illustrated.

As illustrated in FIG. 8, as the cooling period increases, DNA amplification and primer annealing increase, and thus a sufficient band intensity is shown from a cooling period of 20 seconds or more.

Figure 9:
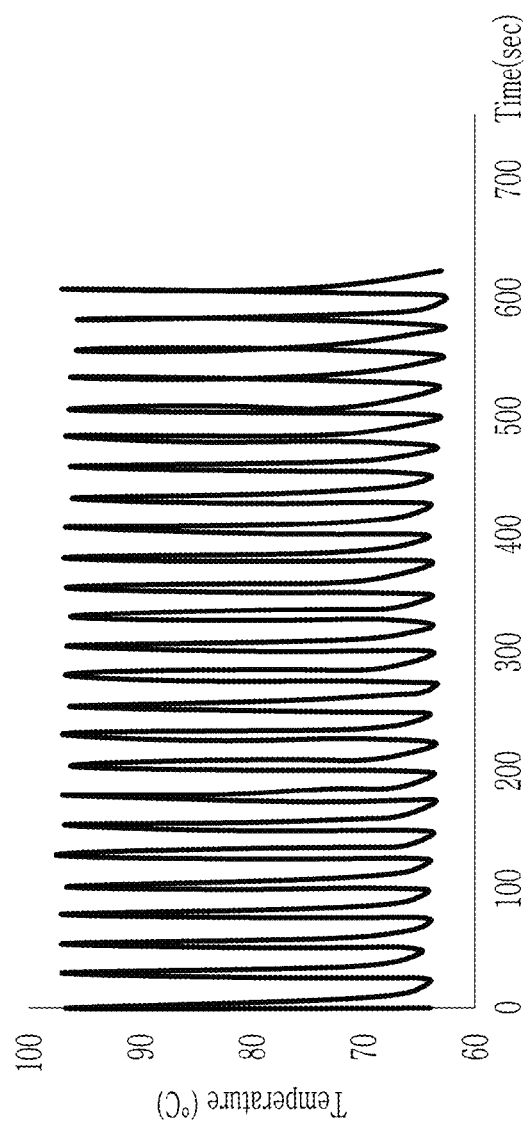
FIG. 9 is a graph showing temperatures in the reaction pad in photothermal PCR amplification at 25 cycles of temperature circulation when the cooling period is 20 seconds.

FIG. 9 is a graph showing temperatures in the reaction pad in photothermal PCR amplification at 25 cycles of temperature circulation when the cooling period is 20 seconds.

As illustrated in FIG. 9, the temperature inside the reaction pad 30 is increased by irradiating the laser to the gold thin film 32 during the heating period of 5 seconds, and then, the laser irradiation is stopped during the cooling period of 20 seconds, and the light is immediately turned off for 20 seconds. Then, the temperature inside the reaction pad 30 required for DNA amplification and primer annealing decreases. One cycle of temperature circulation is repeated 25 times. It can be seen that a photothermal PCR amplification product is shown with sufficient band intensity in a short time of total 25 seconds, approximately 10 minutes by repeating a cycle of temperature circulation of 25 seconds 25 times.

Hereinafter, a method for measuring and analyzing a photothermal PCR amplification result will be described with reference to FIGS. 10 to 12.

Figure 10:
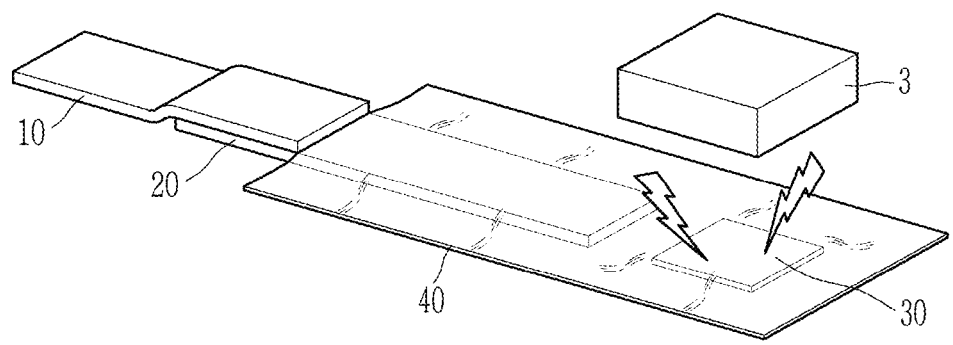
FIG. 10 is a diagram schematically illustrating a fluorescent signal generated from the amplification/detection kit after the photothermal PCR amplification is performed.

FIG. 10 is a diagram schematically illustrating a fluorescent signal generated from the amplification/detection kit after the photothermal PCR amplification is performed.

In FIG. 10, a PCR product for which photothermal PCR amplification is completed may emit light with fluorescence of SYBR™ green. The fluorescence measurement device 3 may measure the photothermal PCR amplification result by measuring the intensity of SYBR™ green fluorescence emitted from the reaction pad 30 of the amplification/detection kit 1.

For example, using primers shown in Table 1 below, photothermal PCR amplification was performed by repeating a temperature circulation cycle of irradiating a 600 mW-intensity 785 nm laser to a 10 nm-thick gold thin film 32 for 5 seconds and stopping for 20 seconds 25 times to isolate and amplify DNA of *Staphylococcus aureus* to be detected.

TABLE 1

| Strain | Primer | Sequence | Sequence number |
|---|---|---|---|
| Staphylococcus aureus | Forward | GCA CAT CTT GAC GGT ACC TAA TC | 1 |
| | Reverse | CGC GCT TTA CGC CCA ATA A | 2 |

At this time, the conditions of the PCR reaction solution are as follows.
  qPCR 2× PreMIX (SYBR™ Green with low ROX) —enzynomics: 5 µl
  Template Solution (*S. aureus* DNA purification—using Qiagen DNA extraction kit): 1 µl
  Forward primer (1 µM): 1 µl
  Reverse primer (1 µM): 1 µl
  Onetaq polymerase (5 kU/ml): 0.5 µl
  DDW: 1.5 µl
  Total: 10 µl In one embodiment, *Staphylococcus aureus* was used as an example of a microorganism, but an embodiment may be equally applied to other types of bacteria and viruses.

Figure 11:
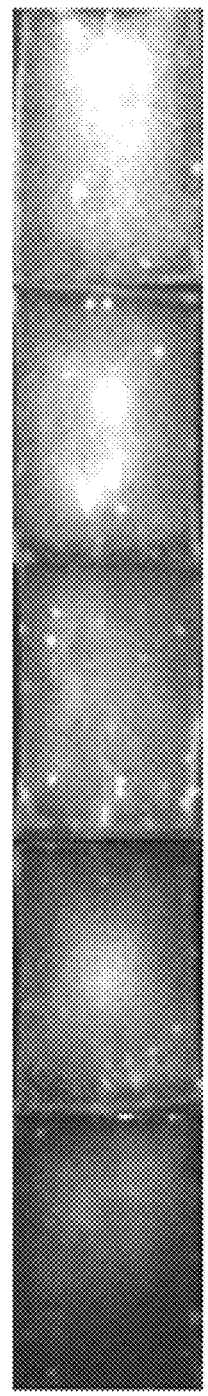
FIG. 11 is a diagram illustrating the intensity of SYBR™ green fluorescence obtained from a fluorescence measuring device according to a concentration of bacteria.

FIG. 11 is a diagram illustrating the intensity of SYBR™ green fluorescence obtained from a fluorescence measuring device according to a concentration of bacteria.

Among the above conditions, the concentration of bacteria may be adjusted to 0.1 pg/µl, 1 pg/µl, 10 pg/µl, or 100 pg/µl by controlling the mass of *S. aureus* DNA contained in a template solution. For example, in the case of 0.1 pg/µl, 1 pg of *S. aureus* DNA was dissolved in 1 µl of the template solution, in the case of 1 pg/µl, 10 pg of *S. aureus* DNA was dissolved in 1 µl of the template solution, and in the case of 10 pg/µl, 100 pg of *S. aureus* DNA was dissolved in 1 µl of the template solution, and in the case of 100 pg/µl, 1000 pg of *S. aureus* DNA was dissolved in 1 µl of the template solution. For reference, in a "control" condition illustrated in FIG. 11, *S. aureus* DNA was not included in the template solution.

Figure 12:
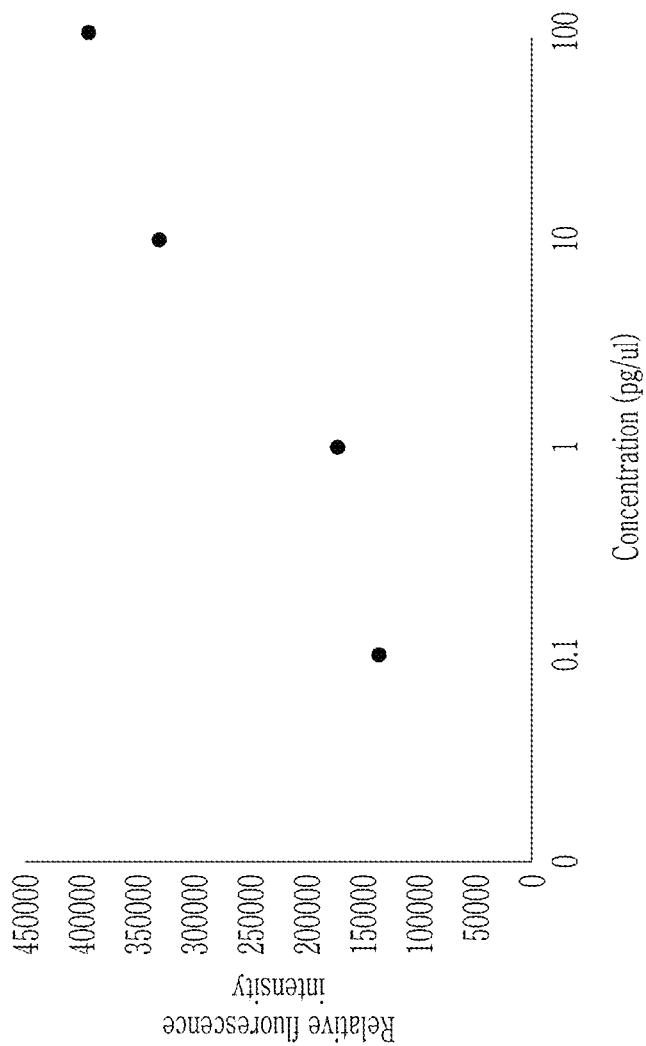
FIG. 12 is a graph showing the intensities of SYBR™ green fluorescence to relative intensities according to various concentrations.

FIG. 12 is a graph showing the intensities of SYBR™ green fluorescence to relative intensities according to various concentrations.

As illustrated in FIG. 12, up to a concentration of 0.1 pg/µl was detected, and this result is a value of at least 10 times higher than a result of confirming a conventional PCR result by gel electrophoresis.

According to an embodiment, the process of confirming the result from the start of the photothermal PCR amplification may be quickly finished in about 14 minutes. Since the PCR amplification may be performed on the pad, various applications are possible. In particular, when combined with paper-based sample pretreatment technology, an all-in-one system may be provided to complete genetic testing in a short time by dramatically shortening the entire genetic testing process.

The heating period, the cooling period, the laser wavelength, and the number of repetitions of temperature circulation described in the embodiment are only specific examples for explaining an embodiment, and the present invention is not limited thereto. The heating period, the cooling period, the laser wavelength, and the number of repetitions of temperature circulation may be appropriately changed according to various conditions to which the amplification/detection kit according to an embodiment is applied.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

DESCRIPTION OF SYMBOLS

1: Amplification/detection kit
10: Sample pad
20: Transfer pad
30: Reaction pad
40: Sealing tape

What is claimed is:

1. A photothermal polymerase chain reaction amplification method using an amplification/detection kit including a gold thin film formed by depositing gold on a pad with an electron-beam, comprising the steps:
   surrounding the gold thin film with a sealing frame to withstand an internal pressure of the pad caused by a high temperature during the photothermal polymerase chain reaction amplification method;
   a first step of irradiating the gold thin film with light having a predetermined intensity and a predetermined wavelength by using a laser configured to radiate the light having the predetermined intensity and the predetermined wavelength for a first period; and
   a second step of irradiating the gold thin film with light having the predetermined intensity and the predetermined wavelength by using the laser for a third period after a second period from an end time point of the first period,
   wherein a further step of irradiating the gold thin film with light having the predetermined intensity and the predetermined wavelength by using the laser is not operated for a fourth period from an end time point of the third period,
   wherein the gold thin film has a thickness of 10 nm and is deposited on a glass fiber of the pad, and
   wherein a photothermal polymerase chain amplification reaction occurs in spaces inside the glass fiber.

2. The photothermal polymerase chain reaction amplification method of claim 1, wherein:
   for the first period and the third period,
   heat is transferred to the pad from the gold thin film to isolate DNA of a microorganism from a polymerase chain reaction solution.

3. The photothermal polymerase chain reaction amplification method of claim 2, wherein:
   for the second period and the fourth period,
   the heat is emitted from the pad and DNA polymerization and primer annealing of the microorganism occur in the polymerase chain reaction solution.

4. A microorganism detection method using an amplification/detection kit including a gold thin film formed by depositing gold on a pad with an electron-beam, comprising the steps:
   surrounding the gold thin film with a sealing frame to withstand an internal pressure of the pad caused by a photothermal polymerase chain reaction amplification process;
   a first step of irradiating the gold thin film with light having a predetermined intensity and a predetermined wavelength by using a laser configured to radiate the light having the predetermined intensity and the predetermined wavelength for a first period;
   a second step of irradiating the gold thin film with light having the predetermined intensity and the predetermined wavelength by using the laser for a third period after a second period from an end time point of the first period; and
   measuring light emitted from the amplification/detection kit after at least the first and second steps of irradiating are terminated,
   wherein the gold thin film has a thickness of 10 nm and is deposited on a glass fiber of the pad, and
   wherein a photothermal polymerase chain amplification reaction occurs in spaces inside the glass fiber.

5. The microorganism detection method of claim 4, wherein:
   for the first period and the third period,
   heat is transferred to the pad from the gold thin film to isolate DNA of a microorganism to be detected from a polymerase chain reaction solution.

6. The microorganism detection method of claim 5, wherein:
   for the second period and the fourth period, the heat is emitted from the pad and DNA polymerization and primer annealing of the microorganism occur in the polymerase chain reaction solution.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Staphylococcus aureus_forward primer

```
<400> SEQUENCE: 1
gcacatcttg acggtaccta atc                                          23

<210> SEQ ID NO 2
<211> LENGTH: 19
<212> TYPE: DNA
<213> ORGANISM: Artificial Sequence
<220> FEATURE:
<223> OTHER INFORMATION: Staphylococcus aureus_reverse primer

<400> SEQUENCE: 2
cgcgctttac gcccaataa                                               19
```